United States Patent [19]
Freud

[11] Patent Number: 6,020,960
[45] Date of Patent: Feb. 1, 2000

[54] SYSTEM FOR THE IN-LINE EXTRACTION AND DILUTION OF A REPRESENTATIVE SAMPLE OF A PROCESSED MEDIUM

[75] Inventor: Paul J. Freud, Furlong, Pa.

[73] Assignee: Honeywell Inc., Minneapolis, Minn.

[21] Appl. No.: 09/030,463

[22] Filed: Feb. 25, 1998

[51] Int. Cl.[7] ........................... G01N 15/02; G01N 21/00
[52] U.S. Cl. ........................ 356/336; 356/335; 356/337; 356/338; 356/73
[58] Field of Search .................................. 356/336, 335, 356/337, 338, 73

[56] References Cited

U.S. PATENT DOCUMENTS

| | | |
|---|---|---|
| 3,822,095 | 7/1974 | Hirschfeld . |
| 5,062,713 | 11/1991 | Farquharson et al. . |
| 5,074,158 | 12/1991 | Tokoyama . |
| 5,274,431 | 12/1993 | Kuroda . |
| 5,287,168 | 2/1994 | Poucher et al. . |
| 5,416,580 | 5/1995 | Trainer . |
| 5,568,266 | 10/1996 | Ciza et al. . |
| 5,757,476 | 5/1998 | Nakamoto et al. . |
| 5,801,820 | 9/1998 | Bysouth et al. . |

Primary Examiner—Frank G. Font
Assistant Examiner—Roy M. Punnoose
Attorney, Agent, or Firm—Anthony Miologos

[57] ABSTRACT

A system is disclosed for the extraction and delivery of a diluted representative sample of a processed medium, flowing as a process stream in a conduit, for the analysis by a particle measurement instrument. The system includes a shroud tube located within the conduit, longitudinally aligned with the process stream and arranged to receive and allow a portion of the process stream to flow therethrough. A diluent delivery apparatus includes an emitter that is located in the shroud tube arranged to release a stream of diluent into the shroud tube. The diluent released by the emitter mixes with the processed medium within the shroud tube. A sample recirculation apparatus is connected to the particle measurement instrument and includes a collector located in the shroud tube downstream from the emitter and a drain located in the conduit downstream of the collector. The collector captures representative samples of the diluted processed medium flowing past the collector and conveys, on a continual basis, the captured samples to the particle measurement instrument for analysis. The representative samples displaced by the newly arriving samples are conveyed to the drain and returned to the process stream flowing in the conduit. The flow of the diluent from the emitter can be adjusted by manipulating a flow control device. The flow control device can be adjusted manually or automatically by the controlling output of a controller responsive to output signals from the particle measurement instrument.

11 Claims, 2 Drawing Sheets

SYSTEM FOR THE IN-LINE EXTRACTION AND DILUTION OF A REPRESENTATIVE SAMPLE OF A PROCESSED MEDIUM

CROSS-REFERENCE TO RELATED APPLICATIONS

The present application is related to co-pending application, Ser. No. 09/030,239, "IN-LINE DILUTING EXTRACTOR", filed on the same date herewith, and having a common assignee to the present invention.

FIELD OF THE INVENTION

This invention relates generally to the field of particle size distribution analysis and more particularly to a system for the in-line extraction, dilution and conveyance of a representative sample of a processed medium for examination by a particle size distribution measurement instrument.

BACKGROUND OF THE INVENTION

Particle size distribution is an important parameter in many processes and its accurate measurement is required for the precise and cost-effective control of the process. The measurement of particle size distribution in order to accurately control a process finds importance in industries that manufacture cement, cosmetics, pharmaceuticals and the like. A number of instruments are presently used in industry that use angular light scattering or dynamic light scattering techniques to measure particle size distribution in a liquid medium. These instruments analyze and measure the concentration of particles suspended in the liquid medium and provide a measurement that is used to adjust the process in order to correct for any irregularities in the final processed product. One such angular light scattering measurement instrument is taught in U.S. Pat. No. 5,416,580, to Trainer et al, issued May 16, 1995.

In order for these aforementioned instruments to measure correct particle size distribution, an extracted sample representative of the processed medium must be conditioned for measurement. Conditioning disperses the particles within the suspension into a concentration value that is within the concentration requirements of the measurement technique being utilized. The concentration of particles within a typical process is generally higher than is allowed by the measurement technique being utilized and the aforementioned conditioning introduces some form of dilution to disperse the concentration. For example, in the case of instruments that employ angular light scattering techniques, multiple scattering limits the concentration to less than 0.1% of particles in suspension. In the case of dynamic light scattering, particle-to-particle interactions limit concentration to less than 3%. Particle concentrations in a processed medium, however, can be as high as 50% by volume.

One method presently employed that overcomes these limitations is to deliver an extracted sample representative of the processed medium to a conditioning instrument, which works in association with the measurement instrument and dilutes, disperses and finally circulates the conditioned sample to the measurement instrument for analysis. After analysis, the diluted sample is discarded and the cycle repeated. Such conditioning instruments are taught in U.S. Pat. No. 4,496,244. to Ludwig et al, issued Jan. 29, 1985, and U.S. Pat. No. 5,439,288, to Hoffman et al, issued Aug. 8, 1995.

These arrangements have shortcomings in the need to transport a concentrated sample from the process location to the conditioning instrument, the time involved in the conditioning-circulating-flushing cycle and the final discarding of the dilute sample in preparation for the next sample extraction. Such conditioning instruments also suffer from poor reliability and excessive maintenance due inherently to the mechanical actions and motions of the multiple seals, valves and conduits that are required to extract the sample from the processed medium, condition the extracted sample and finally deliver the sample to the measurement instrument.

SUMMARY OF THE INVENTION

Therefore, there is provided by the present invention a system for the extraction and delivery of a diluted representative sample of a processed medium, flowing as a process stream within a conduit or pipe, for the analysis by a particle measurement instrument. The system of the present invention includes a shroud tube located within the conduit, longitudinally aligned with the process stream and arranged to receive and allow a portion of the process stream to flow therethrough.

A diluent delivery arrangement includes an emitter that is located in the shroud tube. The emitter is arranged to release a stream of diluent into the process stream flowing in the shroud tube. The diluent released by the emitter mixes with the processed medium within the shroud tube, forming a stream of diluted processed medium that flows downstream of the emitter.

A sample recirculation arrangement is connected to the particle measurement instrument and includes a collector located in the shroud tube downstream from the emitter and a drain located in the conduit downstream of the collector. The collector is arranged to capture representative samples of the diluted processed medium flowing past the collector and responsive to the process stream flowing in the shroud tube the representative samples captured are conveyed on a continual basis to the particle measurement instrument for analysis. The representative samples displaced by the newly arriving samples are conveyed to the drain and returned to the process stream flowing in the conduit.

The diluent delivery arrangement further includes a flow control device connected to the emitter and to a source of diluent. The flow control device is arranged to be manipulated to connect the source of diluent to the emitter and to control the amount of diluent released by the emitter into the shroud tube. This flow control device can either be manually manipulated to adjust the flow of diluent to the emitter or adjusted by a controller operatively connected to the flow control device.

The controller is arranged to receive output signals from the measurement instrument representing the dilution concentration of the representative sample under analysis. Responsive to the output signals received from the measurement instrument, the controller develops and applies a controlling output to the flow control device. The controlling output can be effected by a mechanical linkage between the controller and the flow control device or an electrical output signal. The electrical output signal would be applied to an electrically-driven servo actuator or pneumatically-driven actuator that adjusts the flow control device and, therefore, the flow of diluent delivered by the emitter.

Accordingly, it is an object of the present invention to provide a sample delivery and conditioning system that delivers to a measurement instrument a conditioned sample representative of the particles present in a processed medium, on a continual basis, for a real-time, in-situ, measurement analysis of the particle size distribution present in the processed medium without the time limitations imposed by the prior art systems.

It is another object of the present invention to provide a sample delivery and conditioning system that requires no mechanical pumping, seals, gate valves or mechanically-driven recirculating systems and, therefore, requires a minimal effort to operate and to maintain.

It is still another object of the present invention to provide an effective and simple sample delivery and conditioning system that can be used with any number of particle size distribution measurement instruments to effect the precise and cost-effective control of a processed medium.

BRIEF DESCRIPTION OF THE DRAWINGS

Other objects, features, and advantages of the present invention will be apparent from the following description of a preferred embodiment thereof, taken in conjunction with the accompanying drawings, in which.

DETAILED DESCRIPTION OF THE INVENTION

Figure 1:
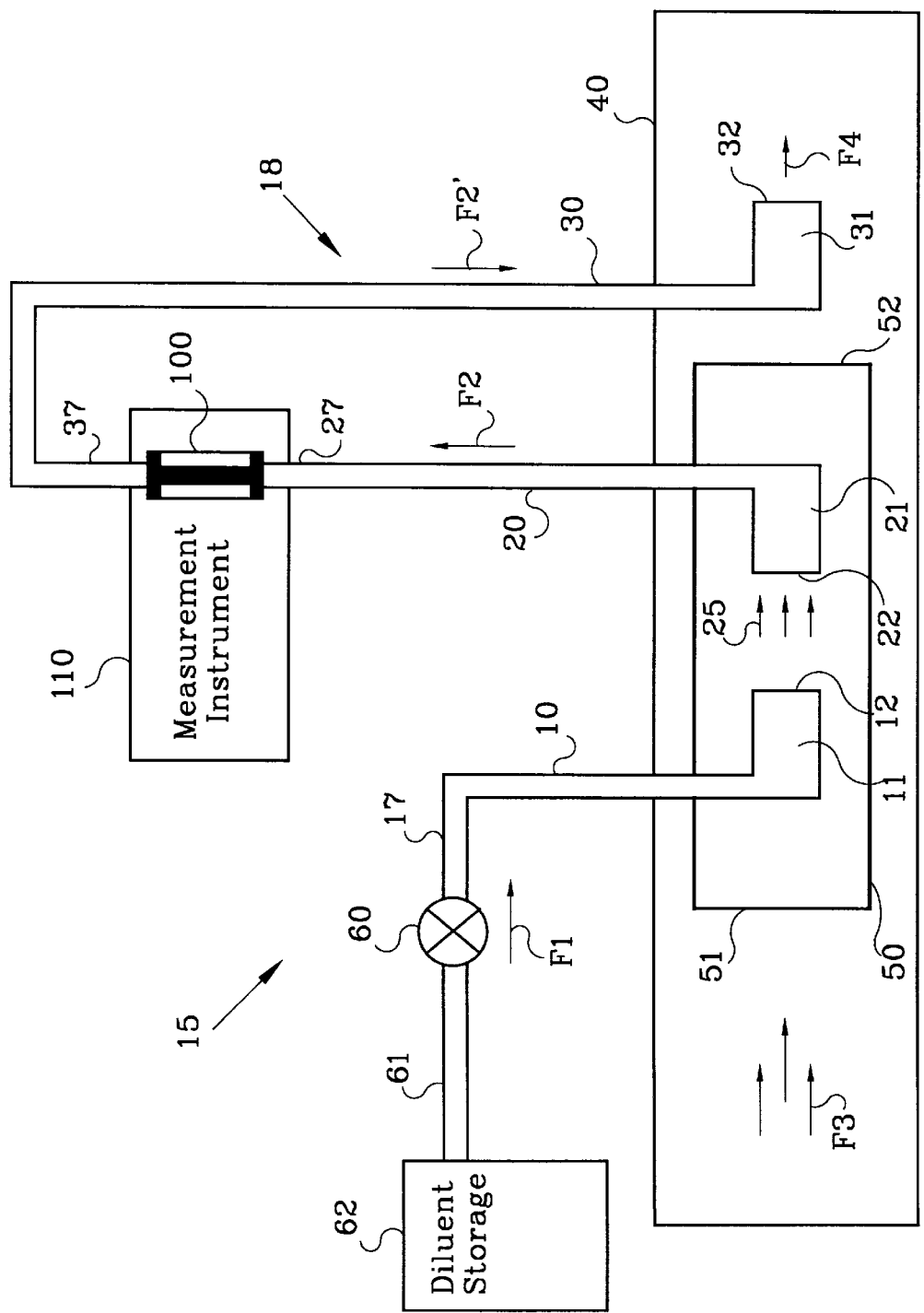
FIG. 1 is a schematic block diagram of the system of the present invention for the in-line extraction, dilution and conveyance of a representative sample of a processed medium for examination by a particle size distribution measurement instrument.
Figure 2:
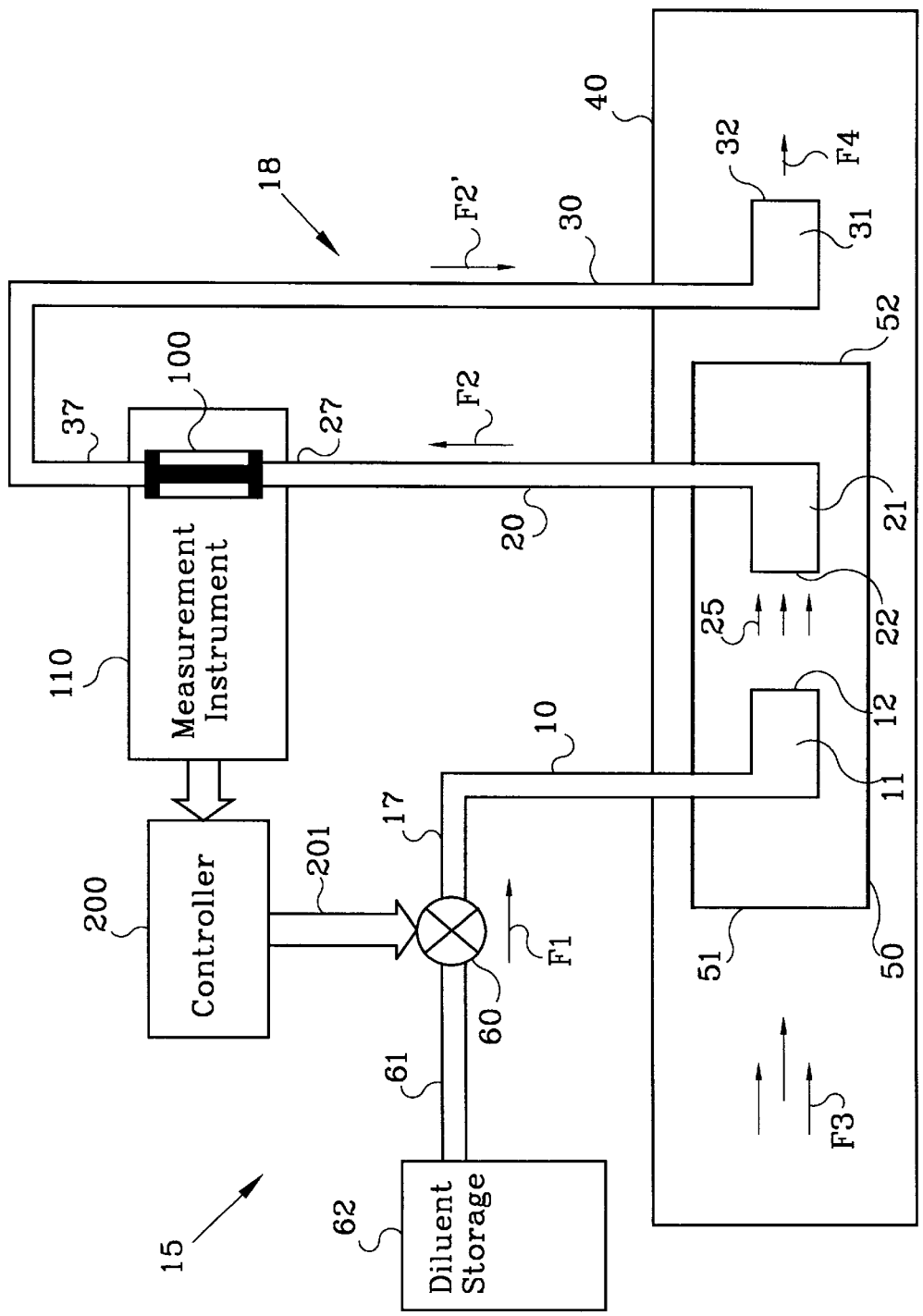
FIG. 2 is a schematic block diagram of the system of FIG. 1 including provisions for automating the dilution of the representative sample extracted from the processed medium.

Turning to FIG. 1, there is shown a system for the in-line extraction, dilution and conveyance of a representative sample of a processed medium in accordance to the present invention. The system is comprised of a diluent delivery arrangement 15 and a sample recirculating arrangement 18. The diluent delivery arrangement 15 includes a diluent delivery conduit 10 having an emitter 11 connected on one end and to a flow control device 60 on an opposite end. Flow control device 60 is connected via conduit 61 to a source of diluent or dilution medium stored in a storage device 62. The sample recirculation arrangement includes a sample delivery conduit 20 connected to a collector 21 on one end and to a sampling cell 100 of a measurement instrument 110 on an opposite end. A sample return conduit 30 connects sampling cell 100 to drain 31. The system of the present invention is contemplated to be used to extract representative samples of a processed medium flowing in a process stream within a pipe or conduit 40. Pipe 40 can either be a main conduit that transports the processed medium during a process operation or a by-pass line that shunts a portion of the processed medium from the main conduit. The processed medium flows within pipe 40 as a process stream in the direction shown by flow arrows F3. A shroud tube 50 is located within pipe 40 in longitudinal alignment with the process stream. Shroud tube 50 receives and channels a portion of the process stream flowing through pipe 40 through a first open end 51 and out of shroud tube 50 via a second open end 52.

Conduit 10 and emitter 11 forms a pitot-like device that is located substantially within shroud tube 50 in proximity to open end 51. Emitter 11 further includes an opening 12 that faces in the direction of the process stream flowing in shroud tube 50. Similarly, conduit 20 and collector 21 of the sample recirculating system form a pitot-like device that is located substantially within shroud tube 50 proximate shroud tube second end 52. Collector 21 further includes an opening 22. However, opening 22 faces against the direction of the process stream flowing within shroud tube 50. As can be seen in FIG. 1, emitter 11 is located within shroud tube 50 upstream, and spaced a distance from, collector 21 which is located in shroud tube 50 at second location downstream of emitter 11. The space within shroud tube 50 between emitter 11 and collector 21 forms mixing region 25. Additionally, opening 12 of emitter 11 faces and is in direct horizontal alignment with opening 22 of collector 21.

Tube 30 and drain 31 of the sample recirculating arrangement forms a pitot-like device that is located within pipe 40 downstream of shroud tube opening 52. Drain 31 further includes an opening 32 that faces in the direction of the process stream flowing in pipe 40.

Sample delivery conduit 20 and sample return conduit 30 each have their opposite ends 27, 37 respectively, terminating at a sampling cell 100 of a measurement instrument 110. Measurement instrument 110 is a device of the type commonly used in particle size distribution measurement and analysis and that employs angular light scattering or dynamic light scattering techniques to measure particle size distribution. In such instruments a conditioned sample representing the processed medium is deposited in sampling cell 100, whereby the measurement instrument performs the measurement and analysis on the conditioned sample contained in the sampling cell. A better understanding of such an instrument and the method used for measurement and analysis may be had by reference to U.S. Pat. No. 5,416,580, to Trainer et al, issued May 16, 1995.

Diluent delivery conduit 10 has an opposite end 17 terminating at the flow control device 60. Flow control device 60 can be a manually adjustable valve, petcock or other such device that can open, close or regulate the flow of diluent flowing through device 60. A dilution medium is stored in the diluent storage device 62 and is conveyed to flow control device 60 via conduit 61.

With renewed reference to FIG. 1, an explanation of the operation of the sample recirculation arrangement will now be given. A processed medium flowing in a process stream through pipe 40 in the direction shown by arrows F3 enters opening 51 of shroud tube 50, where it enters opening 22 of collector 21. The pressure force exerted by flow F3 drives a continuous stream of processed medium into opening 22 of collector 21. The processed medium travels through sample delivery conduit 20 in the direction shown by flow arrow F2, thereby filing sampling cell 100. This continuous stream flowing within conduit 20 replaces the processed medium previously delivered to sampling cell 100. The processed medium forced out of sampling cell 100 by the newly arriving processed medium is returned to pipe 40 in the direction shown by flow arrow F2' via sample return conduit 30 to drain 31. The returned processed medium exits drain 31 from opening 32 and rejoins the main body of the process stream as shown by flow arrow F4.

As it will be understood by those skilled in the art, the arrangement just described illustrates a means of conveying on a continual, real-time basis a concentrated sample of the processed medium to the measurement instrument 110 for analysis. However, as was previously explained, in order for the measurement instrument to correctly measure particle size distribution, the representative sample must be conditioned. Conditioning introduces some form of dilutant or clear suspending medium fluid to disperse the concentration. The dilution is accomplished by the introduction of a diluent medium to the processed medium before it is driven to the sampling cell 100.

With renewed reference to FIG. 1, the operation of the diluent delivery arrangement of the present invention will now be given. Opening flow control device 60 allows the introduction of diluent from storage device 62 via conduit 61, to flow control device 60. The diluent flows through flow control device 60 in the direction of flow arrow F1 into diluent delivery conduit 10. The diluent is carried by conduit 10 to emitter 11, where it exits from opening 12. Any convenient method for extracting the diluent from storage device 61 can be employed, including, but not limited to, motor driven pumps or gravity feed. The process stream flowing in the shroud tube 50 and the diluent medium exiting opening 12 are combined and mixed at mixing region 25, thereby forming a conditioned or diluted representative sample of the processed medium. This conditioned sample is driven by the process stream flowing in shroud tube 50 downstream of emitter 11 toward collector 21. Opening 21 receives the now diluted representative sample, whereby it is conveyed to sampling cell 100 in the manner explained above in the operation of the sample recirculating arrangement. The diluted representative samples are continually conveyed to sampling cell 100, whereby a newly arriving diluted sample displaces a previously deposited diluted sample. The displaced diluted sample exits sampling cell 100 at 37 and is driven through sample extraction conduit 30, where it exits from opening 32 of drain 31 and back into pipe 40 downstream of shroud tube 50.

With a zero flow rate of diluent the sample delivered to sampling cell 100 will be at full concentration. Inversely, with a high rate of diluent flow, greater than the flow of processed medium flowing through shroud tube 50, only diluent will enter opening 22 and the particle concentration of the representative sample reaching sampling cell 100 will be zero. Therefore, by adjusting the flow F1 of diluent through device 60, the concentration of the representative sample delivered to the sampling cell 100 can be controlled. A proper concentration of particles to diluent is required for an accurate measurement by measurement instrument 110. By reading the measure of loading or attenuation from the measurement instrument 110, the flow control device 60 can be manipulated manually to control the flow of diluent. This manual manipulation of the concentration, however, requires the constant attention of the measurement device output by an operator and the manual adjustment of the flow control device 60.

Turning now to FIG. 2, the arrangement illustrated in FIG. 1 is shown including a means for automating the control of diluent to emitter 11. The introduction of diluent into the diluent delivery arrangement taught and shown by FIG. 1 can be effectively automated by connecting the signals representing the loading or attenuation of measurement instrument 100 to a controller device 200. The controller device receives the signals output by the measurement instrument 100, interprets the signals received and develops a controlling output 201 to flow control device 60. The controlling output 201 can be effected by a mechanical linkage between controller 201 and flow control device 60 or an electrical output signal. The electrical output signal would be applied to an electrically-driven servo actuator or pneumatically-driven actuator (not shown), that adjusts the opening of flow control device 60 and, therefore, the flow F1 delivered by emitter 11. In this manner, the arrangement of the present invention will continuously provide a correct conditioned sample to measurement instrument 110 irrespective of the size or concentration of the particles in the processed medium or the flow pressure or rate of flow of the process stream.

The arrangement of the present invention provides a sample delivery system that requires no mechanical pumping, seals, gate valves or reticulating systems and, therefore, requires a minimal effort to operate and to maintain. Additionally, the present invention delivers to the measurement instrument 110 a conditioned sample representative of the particles present in a processed medium on a continual basis for a real-time, in-situ measurement analysis without the time limitations imposed by the prior art systems. Finally, the conditioning and delivery system of the present invention provides an effective and simple system that can be used with any number of particle size distribution measurement instruments to effect the precise and cost-effective control of a processed medium.

The present invention has been described with particular reference to the preferred embodiments thereof. It will be obvious that various changes and modifications can be made therein without departing from the spirit and scope of the invention as defined in the appended claims.

What is claimed is:

1. A system for the extraction and delivery of a diluted representative sample of a processed medium, flowing in a process stream, for the analysis by a particle measurement instrument, said system comprising:

a shroud tube located substantially within and longitudinally aligned with said process stream, arranged to receive and allow a portion of said process stream to flow therethrough;

a diluent delivery apparatus including an emitter extending into said shroud tube, said emitter arranged to release a stream of diluent into the process stream flowing in said shroud tube, said diluent mixing with said processed medium, forming a stream of diluted processed medium flowing in said shroud tube downstream of said emitter;

a sample recirculation apparatus connected to said particle measurement instrument, said sample recirculation apparatus including a collector extending into said shroud tube downstream from said emitter, said collector arranged to capture a representative sample of said diluted processed medium flowing past said collector and said sample recirculating apparatus conveying said diluted representative sample to said particle measurement instrument for analysis, said sample recirculation apparatus further including a drain extending into said process stream downstream of said collector, whereby said drain returns said diluted representative sample to said process stream after analysis by said particle measurement instrument.

2. The system as claimed in claim 1, wherein said diluted representative sample is continuous stream of diluted representative samples that are driven through said recirculating apparatus by said process stream.

3. The system as claimed In claim 1, wherein said diluent delivery apparatus includes a flow control device connected to said emitter and to a source of diluent whereby said flow control device is arranged to be manipulated to connect said source of diluent to said emitter and to control the amount of diluent released by said emitter into said process stream.

4. The system as claimed In claim 3, wherein said flow control device is manually manipulated to control the amount of diluent released by said emitter into said process stream.

5. The system as claimed In claim 3, wherein said system further includes a controller operatively connected to said flow control device, said controller arranged to receive output signals from said measurement instrument representing the dilution concentration of the representative sample under analysis and responsive to said output signals received from said measurement instrument to develop and apply an output to said flow control device that manipulates the flow control device to control the amount of diluent released by said emitter into said process stream.

6. The system as claimed in claim 2, wherein said process stream is contained within a conduit.

7. A system for the extraction and delivery of a diluted representative sample of a processed medium, flowing in a process stream, for the analysis by a particle measurement instrument, said system comprising:

a conduit arranged to substantially contain and allow said process stream to flow therethrough;

a housing located within said conduit, longitudinally aligned with said process stream, arranged to receive and allow a portion of said process stream to flow therethrough;

a diluent delivery apparatus including an emitter extending into said housing, said emitter arranged to release a stream of diluent into the process stream flowing in said housing, said diluent mixing with said processed medium, forming a stream of diluted processed medium flowing in said housing downstream of said emitter;

a sample recirculation apparatus connected to said particle measurement instrument, said sample recirculation apparatus including a collector extending into said housing downstream from said emitter and a drain extending into said conduit downstream of said collector, said collector arranged to capture representative samples of said diluted processed medium flowing past said collector and, responsive to said process stream flowing in said housing, said sample recirculating apparatus conveys on a continual basis said diluted representative samples to said particle measurement instrument for analysis, replacing previously conveyed diluted representative samples, whereby said replaced diluted representative samples are conveyed to said drain and returned to said process stream.

8. The system as claimed In claim 7, wherein said diluent delivery apparatus includes a flow control device connected to said emitter and to a source of diluent, whereby said flow control device is arranged to be manipulated to connect said source of diluent to said emitter and to control the amount of diluent released by said emitter into said process stream.

9. The system as claimed In claim 8, wherein said flow control device is manually manipulated to control the amount of diluent released by said emitter into said process stream.

10. The system as claimed In claim 8, wherein said system further includes a controller operatively connected to said flow control device, said controller arranged to receive output signals from said measurement instrument representing the dilution concentration of the representative sample under analysis and, responsive to said output signals received from said measurement instrument, to develop and apply an output to said flow control device that manipulates the flow control device to control the amount of diluent released by said emitter into said process stream.

11. A system for the extraction and delivery of a diluted representative sample of a processed medium, flowing in a process stream, for the analysis by a particle measurement instrument, said system comprising:

means for encompassing receiving and channeling therethrough a portion of said process stream, forming an isolated portion of said processed medium from said processed medium flowing in said process stream;

means for delivering and releasing into said isolated portion a stream of diluent, said diluent mixing with said processed medium forming a stream of diluted processed medium flowing in said isolated portion;

means for extracting arranged to capture representative samples of said diluted processed medium flowing in said isolated portion and responsive to said process stream said means for extracting conveys on a continual basis said diluted representative samples to said particle measurement instrument for analysis; and means for returning arranged to receive from said measurement instrument the representative samples displaced by newly arriving representative samples and return said representative samples displaced to said process stream.

\* \* \* \* \*